(12) United States Patent
Khanmamedova et al.

(10) Patent No.: US 10,501,388 B2
(45) Date of Patent: Dec. 10, 2019

(54) PROCESS FOR PRODUCING BTX FROM A C5—C12 HYDROCARBON MIXTURE

(71) Applicant: SABIC GLOBAL TECHNOLOGIES B.V., Bergen op Zoom (NL)

(72) Inventors: Alla Khanmamedova, Sugar Land, TX (US); Scott A. Stevenson, Houston, TX (US); Dustin Fickel, Richmond, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 11 days.

(21) Appl. No.: 15/749,240

(22) PCT Filed: Aug. 18, 2016

(86) PCT No.: PCT/EP2016/069554
§ 371 (c)(1),
(2) Date: Jan. 31, 2018

(87) PCT Pub. No.: WO2017/032672
PCT Pub. Date: Mar. 2, 2017

(65) Prior Publication Data
US 2018/0230073 A1 Aug. 16, 2018

Related U.S. Application Data

(60) Provisional application No. 62/207,968, filed on Aug. 21, 2015.

(30) Foreign Application Priority Data

Sep. 9, 2015 (EP) ..................... 15184537

(51) Int. Cl.
| | | |
|---|---|---|
| *C07C 4/18* | (2006.01) | |
| *B01J 29/44* | (2006.01) | |
| *C07C 5/13* | (2006.01) | |
| *C07C 5/41* | (2006.01) | |
| *C07C 15/04* | (2006.01) | |
| *C07C 15/06* | (2006.01) | |
| *C07C 15/08* | (2006.01) | |

(52) U.S. Cl.
CPC ............... *C07C 4/18* (2013.01); *B01J 29/44* (2013.01); *C07C 5/13* (2013.01); *C07C 5/41* (2013.01); *C07C 15/04* (2013.01); *C07C 15/06* (2013.01); *C07C 15/08* (2013.01)

(58) Field of Classification Search
None
See application file for complete search history.

(56) References Cited

U.S. PATENT DOCUMENTS

| | | | |
|---|---|---|---|
| 3,433,848 A | 3/1969 | Devins et al. | |
| 3,957,621 A | 5/1976 | Bonacci et al. | |
| 4,218,573 A | 8/1980 | Tabak et al. | |
| 4,320,242 A | 3/1982 | Onodera et al. | |
| 5,968,342 A | 10/1999 | Tsunoda et al. | |
| 6,001,241 A | 12/1999 | Gosling et al. | |
| 6,635,792 B2 * | 10/2003 | Choi ................ | B01J 29/068 208/111.1 |
| 7,186,871 B2 | 3/2007 | Mitchell et al. | |
| 8,202,815 B2 | 6/2012 | Deluga et al. | |
| 8,309,778 B2 | 11/2012 | Wang et al. | |
| 9,068,125 B2 | 6/2015 | Diehl et al. | |
| 9,926,240 B2 * | 3/2018 | Ward .................. | C07C 4/06 |
| 2006/0287564 A1 | 12/2006 | Choi et al. | |
| 2007/0006473 A1 | 1/2007 | Schopf et al. | |
| 2007/0203377 A1 | 8/2007 | Arca et al. | |
| 2009/0272672 A1 | 11/2009 | Arca et al. | |

(Continued)

FOREIGN PATENT DOCUMENTS

| | | |
|---|---|---|
| AU | 198551458 A | 12/1985 |
| WO | 2007055488 A1 | 5/2007 |
| WO | 2008015027 A1 | 2/2008 |

(Continued)

OTHER PUBLICATIONS

Bhirud, "Chances for Innovative Processes at the Interface between Refining and Petrochemistry" Proceedings of the DGMK Conference (2002) 10 Pages.
Kirk-Othmer Encyclopedia of Chemical Technology, "Molecular Sieves," Fifth Edition, vol. 16, (2006), pp. 811-853.
Le Page, "Applied Heterogeneous Catalysis: Design, Manufacture, Use of Solid Catalysts," (1987) Institut Francais due Petrole Publications; pp. 1-7.
Rase, Handbook of Commercial Catalysts: Heterogeneous Catalysts ed. (2000) CRCPRess p. 211-212.

(Continued)

*Primary Examiner* — Philip Y Louie
*Assistant Examiner* — Alyssa L Cepluch
(74) *Attorney, Agent, or Firm* — Cantor Colburn LLP

(57) ABSTRACT

The invention relates to a process for producing benzene comprising the steps of: (a) providing a hydrocracking feed stream comprising $C_5$-$C_{12}$ hydrocarbons, (b) contacting the hydrocracking feed stream in the presence of hydrogen with a hydrocracking catalyst under process conditions including a temperature of 425-580° C., a pressure of 300-5000 kPa gauge and a Weight Hourly Space Velocity of 3-30 $h^{-1}$ to produce a hydrocracking product stream comprising BTX and (c) separating the BTX from the hydrocracking product stream, wherein the hydrocracking catalyst comprises a shaped body comprising a zeolite and a binder and a hydrogenation metal deposited on the shaped body, wherein the amount of the hydrogenation metal is 0.010-0.30 wt-% with respect to the total catalyst and wherein the zeolite is ZSM-5 having a silica ($SiO_2$) to alumina ($Al_2O_3$) molar ratio of 25-75.

17 Claims, No Drawings

(56) References Cited

U.S. PATENT DOCUMENTS

2015/0166434 A1    6/2015  Ward

FOREIGN PATENT DOCUMENTS

WO           2013182534 A1    12/2013
WO      WO-2013182534 A1 *  12/2013  .......... B01J 35/0006
WO           2015128317 A1     9/2015
WO           2016005105 A1     1/2016

OTHER PUBLICATIONS

International Search Report for International Application No. PCT/EP2016/069554; International Filing Date: Aug. 18, 2016; dated Sep. 9, 2016; 6 Pages.

Written Opinion of the International Searching Authority for International Application No. PCT/EP2016/069554; International Filing Date: Aug. 18, 2016; dated Sep. 9, 2016; 7 Pages.

* cited by examiner

PROCESS FOR PRODUCING BTX FROM A C5—C12 HYDROCARBON MIXTURE

CROSS REFERENCE TO RELATED APPLICATIONS

This application is a 371 of International Application No. PCT/EP2016/069554, filed Aug. 18, 2016, which claims priority to European Application No. 15184537.7, filed Sep. 9, 2015 and U.S. Application Ser. No. 62/207,968 filed Aug. 21, 2015 which are incorporated herein by reference in their entirety.

The present invention relates to a process for producing BTX from a mixed feedstream comprising $C_5$-$C_{12}$ hydrocarbons by contacting said feedstream in the presence of hydrogen with a catalyst having hydrocracking activity.

It has been previously described in WO 02/44306 A1 and WO 2007/055488 A1 that aromatic hydrocarbon compounds and LPG can be produced from a mixed hydrocarbon feedstock having boiling points of 30-250° C. Therefore a hydrocarbon feedstock having boiling points of 30-250° C. and hydrogen is introduced to a reaction zone wherein said hydrocarbon feedstock is converted in the presence of a catalyst to aromatic hydrocarbon compounds abundant in BTX through hydrodealkylation and/or transalkylation and to non-aromatic hydrocarbon compounds which are abundant in LPG through hydrocracking and recovering the aromatic hydrocarbon compounds and LPG, respectively, through gas-liquid separation and distillation. The methods of WO 02/44306 A1 and WO 2007/055488 produce a product stream comprising a relatively high amount of non-aromatic hydrocarbons that co-boil with BTX rendering it impossible to produce chemical grade BTX without using solvent extraction methods and a relatively high amount of fuel gas at the expense of the LPG produced.

US2009/0272672 discloses a process for the catalytic hydrodealkylation of $C_8$-$C_{13}$ alkylaromatic compounds mixed with $C_4$-$C_{10}$ aliphatic and cycloaliphatic products which undergo aromatization and subsequent hydrodealkylation. In this process, the hydrocarbons are treated with a ZSM-5 zeolite having the $SiO_2/Al_2O_3$ molar ratio of 5-100 modified by means of a platinum-molybdenum couple at a temperature of 400 to 650° C., a pressure of 2 to 4 MPa and $H_2$/feedstock molar ratio ranging from 3 to 6.

US2006/0287564 describes a process for increasing the production of benzene from a hydrocarbon mixture including separating a hydrocarbon feedstock into a $C_6$ or lower hydrocarbon stream and a $C_7$ or higher hydrocarbon stream. The $C_6$ or lower hydrocarbon stream is separated into a non-aromatic hydrocarbon stream and an aromatic hydrocarbon stream through a solvent extraction process. The $C_7$ or higher hydrocarbon stream is subjected to a reaction in the presence of a catalyst comprising platinum/tin or platinum/lead.

U.S. Pat. No. 3,957,621 describes a process for processing heavy reformates from which benzene and lighter components have been largely removed. The removed stream includes the major portion of the benzene in the charge and can include a substantial portion of the toluene.

WO2013/182534 discloses a process for producing BTX from a $C_5$-$C_{12}$ hydrocarbon mixture using a hydrocracking/hydrodesulphurisation catalyst. According to WO2013/182534, the process results in a mixture comprising substantially no co-boilers of BTX, thus chemical grade BTX can easily be obtained.

While WO2013182534 advantageously provides a chemical grade BTX, there is a demand for a process which produces an effluent having a composition which comprises more amounts of desirable components such as BTX and LPG and less amounts of components such as methane.

It is an object of the present invention to provide a process for converting a $C_5$-$C_{12}$ hydrocarbon feed stream into a product stream comprising BTX in which above and/or other needs are met.

Accordingly, the present invention provides a process for producing benzene comprising the steps of:

(a) providing a hydrocracking feed stream comprising $C_5$-$C_{12}$ hydrocarbons, (b) contacting the hydrocracking feed stream in the presence of hydrogen with a hydrocracking catalyst under process conditions including a temperature of 425-580° C., a pressure of 300-5000 kPa gauge and a Weight Hourly Space Velocity of 3-30 $h^{-1}$ to produce a hydrocracking product stream comprising BTX and (c) separating the BTX from the hydrocracking product stream, wherein the hydrocracking catalyst comprises shaped body comprising a zeolite and a binder and a hydrogenation metal deposited on the shaped body, wherein the amount of the hydrogenation metal is 0.010-0.30 wt-% with respect to the total catalyst and wherein the zeolite is ZSM-5 having a silica ($SiO_2$) to alumina ($Al_2O_3$) molar ratio of 25-75.

It will be appreciated that step (c) of the process provides benzene in the form of a BTX which comprises benzene. It will therefore be appreciated that the above process of the present invention may also be described as a process for producing BTX comprising the steps of:

(a) providing a hydrocracking feed stream comprising $C_5$-$C_{12}$ hydrocarbons, (b) contacting the hydrocracking feed stream in the presence of hydrogen with a hydrocracking catalyst under process conditions including a temperature of 425-580° C., a pressure of 300-5000 kPa gauge and a Weight Hourly Space Velocity of 3-30 $h^{-1}$ to produce a hydrocracking product stream comprising BTX and (c) separating the BTX from the hydrocracking product stream, wherein the hydrocracking catalyst comprises shaped body comprising a zeolite and a binder and a hydrogenation metal deposited on the shaped body, wherein the amount of the hydrogenation metal is 0.010-0.30 wt-% with respect to the total catalyst and wherein the zeolite is ZSM-5 having a silica ($SiO_2$) to alumina ($Al_2O_3$) molar ratio of 25-75.

The inventors surprisingly found that the process according to the invention results in a hydrocracking product stream comprising a low proportion of methane and substantially no co-boilers of BTX at a sufficiently high WHSV. A low proportion of methane means that more valuable components such as $C_2$-$C_4$ hydrocarbons and BTX are present in the hydrocracking product stream. The absence of co-boilers of BTX in the product stream allows obtaining a chemical grade BTX by simple distillation of the product stream. This can be achieved at a relatively high level of WHSV, which means that the desired product can be obtained at a higher rate requiring smaller volume reactor resulting in a smaller CAPEX.

As used herein, the term "$C_n$ hydrocarbons", wherein "n" is a positive integer, is meant to describe all hydrocarbons having n carbon atoms. Moreover, the term "$C_{n+}$ hydrocarbons" is meant to describe all hydrocarbon molecules having n or more carbon atoms. Accordingly, the term "$C_{5+}$ hydrocarbons" is meant to describe a mixture of hydrocarbons having 5 or more carbon atoms.

Step a)

According to step a) of the process according to the invention, a hydrocracking feed stream comprising $C_5$-$C_{12}$ hydrocarbons is provided.

Hydrocracking Feed Stream

The hydrocracking feed stream used in the process of the present invention is a mixture comprising $C_5$-$C_{12}$ hydrocarbons, preferably having a boiling point in the range of 30-195° C. Preferably, the hydrocracking feed stream mainly comprises $C_6$-$C_8$ hydrocarbons.

The hydrocracking feed stream may be provided by providing a fresh feed stream and optionally mixing it with another stream, such as a stream recycled from the hydrocracking product stream, such as toluene if desired. This mixing with another stream is optional. If mixing with e.g. a recycle stream does not take place, the hydrocracking feed stream is the same as the fresh feed stream. Suitable examples of fresh feed streams include, but are not limited to first stage or multi-stage hydro-treated pyrolysis gasoline, straight run naphtha, hydrocracked gasoline, light coker naphtha and coke oven light oil, FCC gasoline, reformate or mixtures thereof, which have optionally been subjected to treatments such as hydrogenation, enrichment of mono-aromatic compounds and/or depentanisation.

For instance, a typical composition of first stage hydro-treated pyrolysis gasoline may comprise 10-15 wt % $C_5$ olefins, 2-4 wt % $C_5$ paraffins and cycloparaffins, 3-6 wt % $C_6$ olefins, 1-3 wt % $C_6$ paraffins and naphthenes, 25-30 wt % benzene, 15-20 wt % toluene, 2-5 wt % ethylbenzene, 3-6 wt % xylenes, 1-3 wt % trimethylbenzenes, 4-8 wt % dicyclopentadiene, and 10-15 wt % $C_{9+}$ aromatics, alkylstyrenes and indenes; see e.g. Table E3.1 from Applied Heterogeneous Catalysis: Design, Manufacture, and Use of Solid Catalysts (1987) J. F. Le Page.

It is preferred that the non-aromatic species comprised in the hydrocracking feed stream are saturated (e.g. by the prior hydrogenation) in order to reduce the exotherm within the catalyst bed containing the hydrocracking catalyst used in the present process. Accordingly, preferably, the fresh feed stream is a stream which has been hydrogenated. The hydrogenation advantageously has a further function of hydrodesulphurisation. This is advantageous in that the resulting fresh feed stream has a low sulphur content. The low sulphur content in the fresh feed stream is advantageous in that the hydrocracking catalyst used according to the invention does not need to have a hydrodesulphurisation function.

The fresh feed stream or the hydrocracking feed stream used in the process of the present invention may comprise up to 300 wppm of sulphur (i.e. the weight of sulphur atoms, present in any compound, in relation to the total weight of the feed).

In some embodiments, the fresh feed stream used in the process of the present invention is a stream which has been treated to be enriched in mono-aromatic compounds. As used herein, the term "mono-aromatic compound" relates to a hydrocarbon compound having only one aromatic ring. Means and methods suitable to enrich the content of mono-aromatic compounds in a mixed hydrocarbon stream are well known in the art such as the Maxene process; see Bhirud (2002) Proceedings of the DGMK-conference 115-122.

In some embodiments, the fresh feed stream used in the process of the present invention has been depentanised. Preferably, the fresh feed stream comprises at most 5 wt % of $C_5$ hydrocarbons, more preferably at most 4 wt %, at most 3 wt %, at most 2 wt %, at most 1 wt %, or $C_5$ hydrocarbons.

Preferably, the hydrocracking feed stream is provided by a process which does not involve the step of removing benzene or removing $C_6$ hydrocarbons. This means that intentional removal of benzene has not been performed in providing the hydrocracking feed stream or the fresh feed stream. The step of removing benzene typically induces the removal of coboilers of benzene. According to the present invention, the benzene coboilers present in the hydrocracking feed stream are advantageously converted to useful LPG.

Preferably, the hydrocracking feed stream may comprise at least 10 wt % of benzene, for example at least 20 wt % of benzene, at least 30 wt % of benzene or at least 40 wt % of benzene, and/or at most 90 wt % of beznene, for example at most 80 wt %, at most 70 wt %, at most 60 wt % or at most 50 wt % of benzene.

Preferably, the fresh feed stream may comprise at least 10 wt % of benzene, for example at least 20 wt % of benzene, at least 30 wt % of benzene or at least 40 wt % of benzene, and/or at most 90 wt % of beznene, for example at most 80 wt %, at most 70 wt %, at most 60 wt % or at most 50 wt % of benzene.

Step b)

According to step b) of the process according to the invention, the hydrocracking feed stream is contacted in the presence of hydrogen in a hydrocracking reactor with a hydrocracking catalyst.

The product produced by the hydrocracking step of the process of the present invention (hydrocracking product stream) comprises LPG, BTX and methane.

The term "LPG" as used herein refers to the well-established acronym for the term "liquefied petroleum gas". LPG generally consists of a blend of $C_2$-04 hydrocarbons i.e. a mixture of $C_2$, $C_3$, and $C_4$ hydrocarbons.

The term "BTX" as used herein is well known in the art and relates to a mixture of benzene, toluene and xylenes.

As used herein, the term "chemical grade BTX" relates to a hydrocarbon mixture comprising less than 5 wt % hydrocarbons other than benzene, toluene and xylenes, preferably less than 4 wt % hydrocarbons other than benzene, toluene and xylenes, more preferably less than 3 wt % hydrocarbons other than benzene, toluene and xylenes, and most preferably less than 2.5 wt % hydrocarbons other than benzene, toluene and xylenes.

Furthermore, the "chemical grade BTX" produced by the process of the present invention comprises less than 1 wt % non-aromatic $C_{6+}$ hydrocarbons, preferably less than 0.7 wt % non-aromatic $C_{6+}$ hydrocarbons, more preferably less than 0.5 wt % non-aromatic $C_{6+}$ hydrocarbons and most preferably less than 0.2 wt % non-aromatic $C_{6+}$ hydrocarbons. The most critical contaminants are the non-aromatic species which have boiling points close to benzene including, but not limited to, cyclohexane, methylcyclopentane, n-hexane, 2-methylpentane and 3-methylpentane.

Accordingly, the hydrocracking product stream is substantially free from non-aromatic $C_{6+}$ hydrocarbons. As meant herein, the term "hydrocracking product stream substantially free from non-aromatic $C_6$, hydrocarbons" means that said hydrocracking product stream comprises less than 1 wt % non-aromatic $C_{6+}$ hydrocarbons, preferably less than 0.7 wt % non-aromatic $C_{6+}$ hydrocarbons, more preferably less than 0.5 wt % non-aromatic $C_{6+}$ hydrocarbons and most preferably less than 0.2 wt % non-aromatic $C_{6+}$ hydrocarbons.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

The hydrocracking product stream produced in the process of the present invention preferably comprises less than 5 wt % of methane. Preferably, the hydrocracking product stream produced in the process of the present invention comprises less than 4 wt % of methane, more preferably less than 3 wt % methane, even more preferably less than 2 wt % methane, even more preferably less than 1.5 wt % methane, even more preferably less than 1.4 wt % methane, even more preferably less than 1.3 wt % methane, even more preferably less than 1.2 wt % methane, even more preferably less than 1.1 wt % methane, and most preferably less than 1 wt % methane.

Preferably, the hydrocracking product stream is also substantially free from $C_5$ hydrocarbons. As meant herein, the term "hydrocracking product stream substantially free from $C_5$ hydrocarbons" means that said hydrocracking product stream comprises less than 1 wt % $C_5$ hydrocarbons, preferably less than 0.7 wt % $C_5$ hydrocarbons, more preferably less than 0.6 wt % $C_5$ hydrocarbons and most preferably less than 0.5 wt % $C_5$ hydrocarbons.

It is a particular advantage of the method of the present invention that the hydrocracking product stream is substantially free from non-aromatic $C_{6+}$ hydrocarbons as these hydrocarbons usually have boiling points close to the boiling point of $C_{6+}$ aromatic hydrocarbons. Hence, it can be difficult to separate the non-aromatic $C_{6+}$ hydrocarbons from the aromatic $C_{6+}$ hydrocarbons comprised in the hydrocracking product stream by distillation.

Process Conditions

The process conditions under which the hydrocracking of the feedstream is performed are an important determinant for the composition of the hydrocracking product stream.

In general, when the space velocity is too high, not all co-boilers of BTX are hydrocracked, so it will not be possible to obtain a chemical grade BTX by simple distillation of the product stream. However, at too low space velocity the yield of methane rises at the expense of propane and butane. Also, a higher space velocity requires smaller reactor volumes and thus a lower CAPEX. Hence, it is advantageous to perform the process of the invention at a high space velocity at which substantially all co-coilers of BTX are hydrocracked.

It was found that the hydrocracking step (b) can advantageously be performed at a high space velocity while allowing substantially all co-boilers of BTX to be hydrocracked, due to the high activity of the catalyst. In the catalyst used in the process of the invention, without wishing to be bound by theory, the hydrogenation metal and the zeolite are in close proximity to one another which translates into a shorter diffusion length between the two sites. This allows BTX co-boilers to be hydrocracked at a high space velocity.

Accordingly, in some preferred embodiments, the step (b) is performed at a Weight Hourly Space Velocity (WHSV) of 3-30 $h^{-1}$, for example at least 5 $h^{-1}$, at least 6 $h^{-1}$, at least 7 $h^{-1}$ or at least 8 $h^{-1}$, and/or at most 25 $h^{-1}$, at most 20 $h^{-1}$, at most 15 $h^{-1}$, at most 10 $h^{-1}$. High WHSV such as at least 8 $h^{-1}$ allows particularly small reactor volumes and lower CAPEX.

It has also been found that step (b) can be operated at a relatively low temperature. This allows for greater operational flexibility as well as lower heat duty and may allow longer cycle lengths. Accordingly, in some preferred embodiments, the step (b) is performed at a temperature of 425-445° C. In other embodiments, the step (b) is performed at a temperature of 450-580° C. The higher temperature range results in a high hydrocracking conversion rate.

The hydrocracking of the feedstream is performed at a pressure of 300-5000 kPa gauge, more preferably at a pressure of 600-3000 kPa gauge, particularly preferably at a pressure of 1000-2000 kPa gauge and most preferably at a pressure of 1200-1600 kPa gauge. By increasing reactor pressure, conversion of $C_{5+}$ non-aromatics can be increased, but higher pressure also increases the yield of methane and the hydrogenation of aromatic rings to cyclohexane species which can be cracked to LPG species. This results in a reduction in aromatic yield as the pressure is increased and, as some cyclohexane and its isomer methylcyclopentane, are not fully hydrocracked, there is an optimum in the purity of the resultant benzene at a pressure of 1200-1600 kPa.

The hydrocracking step is performed in the presence of an excess of hydrogen in the reaction mixture. This means that a more than stoichiometric amount of hydrogen is present in the reaction mixture that is subjected to hydrocracking. Preferably, the molar ratio of hydrogen to hydrocarbon species ($H_2$/HC molar ratio) in the reactor feed is between 1:1 and 4:1, preferably between 1:1 and 3:1 and most preferably between 2:1 and 3:1. A higher benzene purity in the product stream can be obtained by selecting a relatively low $H_2$/HC molar ratio. In this context the term "hydrocarbon species" means all hydrocarbon molecules present in the reactor feed such as benzene, toluene, hexane, cyclohexane, etc. It is necessary to know the composition of the feed to then calculate the average molecular weight of this stream to be able to calculate the correct hydrogen feed rate. The excess amount of hydrogen in the reaction mixture suppresses the coke formation which is believed to lead to catalyst deactivation.

Catalyst

The hydrocracking catalyst used in the process of the present invention comprises a hydrogenation metal and a shaped body comprising a ZSM-5 zeolite and a binder, wherein the hydrogenation metal is deposited on the shaped body. Examples of the shaped bodies include, but are not limited to, spherically or cylindrically shaped pellets, tablets, particles and extrudates. The shaped body typically has an average diameter of about 0.1 mm to about 7 mm, typically 1.4 mm to 3.5 mm. The diameter is usually measured by slide caliper. The shaped body typically has an average length of 3 to 8 mm. The average as used herein is an arithmetic average. One specific example of the shaped body is cylindrically shaped extrudate with an average diameter of about 1.6 mm (1/16 inch) with an average length of extrudates about 3 to 8 mm. In such catalyst, the distance between the hydrogenation metal and the zeolite acid site is less than that in a mixed catalyst of a shaped zeolite body and hydrogenation metal supported on a binder. An example of the latter would be a mixture of ZSM-5 zeolite extrudate and Pt deposited on shaped $Al_2O_3$.

It was further observed that the process of the present invention results in a desirable LPG composition in the hydrocracking product stream. LPG with a high amount of $C_2$ hydrocarbons may generally be more valuable than LPG with a high amount of $C_3$ hydrocarbons. It was observed that the hydrocracking catalyst used in the present invention leads to a higher $C_2$ to $C_3$ ratio compared to a hydrocracking catalyst comprising a mixture of ZSM-5 zeolite extrudate and a hydrogenation metal deposited on shaped binder, when the hydrocracking feed stream is naphtha. Accordingly, the process of the present invention wherein the hydrocracking feed stream is naphtha can be advantageously used for producing a hydrocracking product stream comprising a high $C_2$ to $C_3$ ratio.

Zeolites are well-known molecular sieves having three dimensional structures with well-defined channels, pores, cavities with defined pore size. As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001). ZSM-5 zeolite is a medium pore size zeolite having a pore size of about 5-6 Å. ZSM-5 zeolite is a 10-member ring zeolite, i.e. the pore is formed by a ring consisting of 10 $[SiO_4]$ and $[AlO_4]^-$ tetrahedra. ZSM-5 zeolite is a well-known zeolite having MFI structure. The negative charge arising from $[AlO_4]^-$ is neutralized by cation in the zeolite.

The silica ($SiO_2$) to alumina ($Al_2O_3$) molar ratio of the ZSM-5 zeolite is in the range of 25-75.

In the context of the present invention, it was found that using a zeolite having a $SiO_2$ to $Al_2O_3$ molar ratio of 25-75 shows the optimum catalyst performances as measured by activity (as measured by WHSV), contents of benzene and total aromatics (BTX, ethylbenzene (EB) and heavies) and methane in the product stream. Means and methods for quantifying the $SiO_2$ to $Al_2O_3$ molar ratio of a zeolite are well known in the art and include, but are not limited to AAS (Atomic Absorption Spectrometer), ICP (Inductively Coupled Plasma Spectrometry) analysis or XRF (X-ray fluorescence). It is noted that the $SiO_2$ to $Al_2O_3$ molar ratio referred herein is meant as the ratio in the zeolite prior to being mixed with the binder for forming the shaped body. Preferably, the $SiO_2$ to $Al_2O_3$ molar ratio is measured by XRF.

Preferably, the silica to alumina ratio of the ZSM-5 zeolite is in the range of 30-65, more preferably 35-60, more preferably in the range of 40-55. At such ratio, in particular when the silica to alumina ratio is at least 35, the best balance of total aromatics and methane content in the hydrocracking product stream and achievable WHSV for a desired benzene purity is obtained.

The zeolite is in the hydrogen form, i.e. having at least a portion of the original cations associated therewith replaced by $H^+$ ions. Methods to convert an aluminosilicate zeolite to the hydrogen form are well known in the art. A first method involves direct treatment employing an acid for example a mineral acid ($HNO_3$, HCl, etc.). A second method involves direct exchange using an ammonium salt (e.g. $NH_4NO_3$) followed by calcination.

The catalyst used in the process of the present invention comprises 0.010-0.30 wt %, prfeerably 0.010-0.15 wt %, of hydrogenation metal. In the context of the present invention, the term "wt %" when relating to the metal content as comprised in a catalyst relates to the wt % of said metal in relation to the total weight of the hydrogenation metal, the zeolite and the binder. The amount of the hydrogenation metal in the catalyst can be determined e.g. by subjecting the catalyst to XRF.

Preferably, the catalyst comprises 0.015-0.095 wt % of hydrogenation metal. It was found that the catalyst comprising the hydrogenation metal in this range has a particularly high benzene yield. Even more preferably, the catalyst comprises 0.020-0.090 wt %, 0.035-0.080 or 0.040-0.075 wt % of hydrogenation metal. In such ranges, the amount of benzene loss (decrease of amount of benzene in the hydrocracking product stream with respect to the hydrocracking feed stream) by the process of the invention and the amount of methane in the hydrocracking product stream is particularly low. The amount of the total aromatics (BTX, ethylbenzene (EB) and heavies) in the hydrocracking product stream is particularly high.

Preferably, the hydrogenation metal is at least one element selected from Group 10 of the periodic table of Elements or rhodium or iridium. The preferred Group 10 element is palladium and platinum, particularly platinum.

The hydrocracking catalyst used in the process of the invention should have a sufficient hydrogenation activity. Accordingly, it is preferred that the catalyst does not comprise secondary metals, such as tin, lead or bismuth that inhibit the hydrogenation activity of the hydrogenation metal. Preferably, the hydrocracking catalyst used in the process of the present invention accordingly comprises less than 0.01 parts tin and less than 0.02 parts lead and less than 0.01 parts bismuth (on the basis of 100 parts by weight of the total catalyst), preferably less than 0.005 parts tin and less than 0.01 parts lead and less than 0.005 parts bismuth (on the basis of 100 parts by weight of total catalyst).

Further, preferably, the hydrocracking catalyst used in the process of the present invention accordingly comprises less than 0.01 parts molybdenum (on the basis of 100 parts by weight of the total catalyst).

The hydrocracking catalyst comprises a shaped body comprising a ZSM-5 zeolite and a binder. The hydrogenation metal is deposited on the shaped body. The presence of the binder in the shaped body gives adequate crush strength to the catalyst to withstand the pressure in a larger reactor.

The binder material can be inorganic oxide materials. The binder material can comprise an aluminum or silica containing material such as silica, alumina, clay, aluminum phosphate, silica-alumina, or combinations comprising at least one of the foregoing. Alumina ($Al_2O_3$) is a preferred binder. The catalyst can comprise up to 99 wt %, e.g., 1 to 99 wt %, for example 10 to 50 wt % or 20 to 40 wt % of a binder material based on the total weight of the catalyst.

The catalyst may be made by depositing the hydrogenation metal on the shaped body, e.g. by a wet or vapor phase impregnation or by an ion-exchange method. Examples of the preparation method for the catalyst wherein the hydrogenation metal is Pt uses $(NH_3)_4Pt(NO_3)_2$, $(NH_3)_4PtCl_2$ or $(NH_3)_4Pt(OH)_2$ as a platinum source usually in combination with $NH_4Cl$. Another example of the preparation method for the catalyst wherein the hydrogenation metal is Pt uses $H_2PtCl_6$ as a platinum source. The method wherein $H_2PtCl_6$ is used as the platinum source may be preferable in that $NH_4Cl$ is not needed.

Step (c)

The hydrocracking product stream comprises methane, LPG, BTX. The term "LPG" as used herein refers to the well-established acronym for the term "liquefied petroleum gas". LPG generally consists of a blend of $C_2$-$C_4$ hydrocarbons i.e. a mixture of $C_2$, $C_3$, and $C_4$ hydrocarbons. The hydrocracking product stream may be subjected to separation by standard means and methods suitable for separating methane and unreacted hydrogen comprised in the hydrocracking product stream as a first separate stream, the LPG comprised in the hydrocracking product stream as a second separate stream and BTX as a third separate stream. Preferably, the stream comprising BTX is separated from the hydrocracking product stream by gas-liquid separation or distillation.

One non-limiting example of such a separation method of the hydrocracking product stream includes a series of distillation steps. The first distillation step at moderate temperature is to separate most of the aromatic species (liquid product) from the hydrogen, $H_2S$, methane and LPG species. The gaseous stream from this distillation is further cooled (to about $-30°$ C.) and distilled again to separate the remaining aromatics species and most of the propane and butane. The gaseous product (mainly hydrogen, $H_2S$, methane and ethane) is then further cooled (to about $-100°$ C.) to separate the ethane and leave the hydrogen, $H_2S$ and methane in the gaseous stream that will be recycled back to the hydrocracking reactor. To control the levels of $H_2S$ and methane in the reactor feed, a proportion of this recycle gas stream is removed from the system as a purge. The quantity of material that is purged depends on the levels of methane and $H_2S$ in the recycle stream which in-turn depend on the feed composition. As the purge will contain mainly hydrogen and methane it is suitable for use as a fuel gas or may be further treated (e.g. via a pressure swing adsorption unit) to separately recover a high purity hydrogen stream and a methane/$H_2S$ stream which can be used as a fuel gas.

In a further embodiment, the present invention relates to a process for producing benzene from a feedstream comprising $C_5$-$C_{12}$ hydrocarbons, wherein the said process comprises the process for producing BTX of the present invention further comprising the step of contacting BTX (or only the toluene and xylenes fraction of said BTX produced) with hydrogen under conditions suitable to produce a hydrodealkylation product stream comprising benzene and fuel gas.

The conditions suitable to produce a hydrodealkylation product stream comprising benzene and fuel gas are well-known and are described in detail e.g. in WO2013/182534, incorporated herein by reference.

Processes for hydrodealkylation of hydrocarbon mixtures comprising $C_6$-$C_9$ aromatic hydrocarbons include thermal hydrodealkylation and catalytic hydrodealkylation; see e.g. WO 2010/102712 A2. Catalytic hydrodealkylation is preferred in the context of the present invention as this hydrodealkylation process generally has a higher selectivity towards benzene than thermal hydrodealkylation. Preferably catalytic hydrodealkylation is employed, wherein the hydrodealkylation catalyst is selected from the group consisting of supported chromium oxide catalyst, supported molybdenum oxide catalyst, platinum on silica or alumina and platinum oxide on silica or alumina. The process conditions useful for hydrodealkylation, also described herein as "hydrodealkylation conditions", can be easily determined by the person skilled in the art. The process conditions used for thermal hydrodealkylation are for instance described in DE 1668719 A1 and include a temperature of 600-800° C., a pressure of 3-10 MPa gauge and a reaction time of 15-45 seconds. The process conditions used for the preferred catalytic hydrodealkylation preferably include a temperature of 500-650° C., a pressure of 3.5-7 MPa gauge and a Weight Hourly Space Velocity of 0.5-2 $h^{-1}$; see also Handbook of Commercial Catalysts: Heterogeneous Catalysts ed. Howard F. Rase (2004) Loc. cit.

The hydrodealkylation product stream is typically separated into a liquid stream (containing benzene and other aromatics species) and a gas stream (containing hydrogen, $H_2S$, methane and other low boiling point hydrocarbons) by a combination of cooling and distillation. The liquid stream may be further separated, by distillation, into a benzene stream, a $C_7$ to $C_9$ aromatics stream and a heavy aromatic stream. The $C_7$ to $C_9$ aromatic stream, or some part of it, may be fed back to reactor section as a recycle to increase overall conversion and benzene yield. The heavy aromatic stream, which contains polyaromatic species such as biphenyl, is preferably not recycled to the reactor but may be exported as a separate product stream. The gas stream contains significant quantities of hydrogen and may be recycled back, via a recycle gas compressor, to the reactor section. A recycle gas purge may be used to control the concentrations of methane and $H_2S$ in the reactor feed.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

The invention is now elucidated by way of the following examples, without however being limited thereto.

EXAMPLES

Preparation of Hydrocracking Catalyst

Catalysts A-D were prepared by using different HZSM-5 extrudates that were made by using $NH_4$-ZSM-5 zeolite powder having $SiO_2/Al_2O_3$ ratio of about 23, 30, 50 and 80, and alumina ($Al_2O_3$) as binder followed by calcination to form HZSM-5 extrudate. The binder content was about 20 wt % based on the total content of the extrudate. Physical properties of the HZSM-5 extrudate are shown below.

Cylindrical shape, average diameter 1.6 mm
Crush strength (flat plate) 2.2 lb/mm
Compacted bulk density 40 lb/ft$^3$
Surface area, (1-point BET) 375-400 m$^2$/g The zeolite extrudates were obtained from Zeolyst International, Inc. and the as-received zeolite extrudates were further calcined at 550° C. in air. The Pt was added into the zeolite extrudates by an ion-exchange method. The Pt ion-exchange was followed by washing and calcinations of the extrudate.

Catalyst A-D 10.0 g HZSM-5 zeolite extrudates with ZSM-5 having different $SiO_2/Al_2O_3$ ratios (see Table 1 below) were poured into solution of 4.10 g of 0.005 M $H_2PtCl_6.6H_2O$ and 24.58 g of deionized (DI) $H_2O$ in a 500-ml glass flask. Ion-exchange was made at 60° C. with stirring by magnetic stirrer for 24 h. The extrudates were separated from the solution and rinsed with 500 ml water and the rinsing was repeated 5 times. The rinsed extrudates were further washed by stirring with 300 ml water at room temperature for 15 min and were separated. The catalyst was dried at 90° C. (8 h) and then temperature was ramped at 3° C./min to 280° C. and was held for 6 h.

The compositions of the catalysts are summarized below.

TABLE 1

| catalyst | Si, wt % | Al, wt % | Pt, wt % | $SiO_2/Al_2O_3$ Ratio[1] |
|---|---|---|---|---|
| A | 33.65 | 12.62 | 0.02 | 23 |
| B | 33.53 | 13.34 | 0.02 | 30 |
| C | 35.76 | 13.15 | 0.03 | 55 |
| D | 33.54 | 12.11 | 0.03 | 80 |

[1]$SiO_2/Al_2O_3$ ratio of HZSM-5 powder prior to forming extrudate measured by XRF.

The amounts of the elements in the catalysts were determined by X-ray fluorescence (XRF).

Catalyst Testing

Referring to Examples 1 to 11, catalysts described in this application were tested for hydrocracking reaction using stainless steel tube reactor as described below. 0.10 g catalyst (sized 20-40 mesh) was diluted to 3 ml by premixing with SiC (30 grit) and was loaded in a reactor.

Reactor description: ¼" inch tube, 0.028" wall thickness. 1/16" thermocouple with a ⅛" spacer bar; 12"×1" brass over-sleeve; reactor bed is approx. 5-6 inches in length in center of sleeve.

The catalyst was pre-activated (drying, Pt reduction) by subjecting it to 40 standard cubic centimeters (sccm) of $H_2$ per minute at 130° C. under 50 psig for 2 hours and subsequently 40 sccm of $H_2$ (with 50 ppm of $H_2S$) at 350° C. at 50 psig for 30 min.

The hydrocracking feed stream consisted of 70 wt % benzene, 15 wt % 3-methylpentane and 15 wt % methylcyclopentane. All components of the hydrocracking feed stream are Aldrich regent grade chemicals dried under 4 A molecular sieves overnight.

The hydrocracking feed stream was introduced to the reactor at a temperature of 470° C. and a pressure of 200 psig. The molar ratio of $H_2$ to the hydrocarbons was 4 to 1, and the $H_2S$ content was 50 ppm based on the total hydrocarbon and $H_2$ feed.

In all experiments, the WHSV was adjusted to achieve the benzene purity (amount of benzene/amount of benzene plus benzene co-boilers) of 99.82 wt % in the product stream.

Example 1

Catalyst A, weight 0.10 g

Catalyst pretreatment: (a) drying: under 40 sccm $H_2$ at 50 psig at 130° C. for 2 h; (b) subsequent $H_2S$ treatment: 40 sccm of $H_2$ (with 50 ppm of $H_2S$) at 50 psig at 350° C. for 30 min Hydrocarbon feed composition: 70.0 wt % Benzene, 15.0 wt % 3-methylpentane, 15.0 wt % methylcyclopentane Hydrocarbon feed rate varied from 41.2 to 49.4 µl/min to run at WHSV 20.2 to 24.3 $h^{-1}$. $H_2$ (+$H_2S$) rate: varied to maintain $H_2$ to HC molar ratio of 4 to 1, and $H_2S$ content 50 ppm based on total feed Catalyst bed temperature 470° C., pressure 200 psig Example 2

Catalyst B, weight 0.10 g

Catalyst pretreatment: same as described in example 1

Hydrocarbon feed composition and rate: same as described in example 1.

Hydrocarbon feed rate varied from 30.9 to 47.4 µl/min to run at WHSV 15.0 to 23.0 $h^{-1}$.

$H_2$ (+$H_2S$) rate: varied as described in example 1

Catalyst bed temperature 470° C., pressure 200 psig.

Examples 3

Catalyst C, weight 0.10 g

Catalyst pretreatment: same as described in example 1

Hydrocarbon feed composition and rate: same as described in example 1

Hydrocarbon feed rate varied from 18.5 to 20.6 µl/min to run at WHSV 9.0 to 10.0 $h^{-1}$.

$H_2$ (+$H_2S$) rate: varied as described in example 1

Catalyst bed temperature 470° C., pressure 200 psig

Example 4

Catalyst D, weight 0.10 g

Catalyst pretreatment: same as described in example 1

Hydrocarbon feed composition and rate: same as described in example 1.

Hydrocarbon feed rate varied from 4.1 to 8.2 µl/min to run at WHSV 1.98 to 3.96 $h^{-1}$.

$H_2$ (+$H_2S$) rate: varied as described in example 1

Catalyst bed temperature 470° C., pressure 200 psig

TABLE 2

| | | wt % | | C% in effluent | | | |
|---|---|---|---|---|---|---|---|
| Example | Catalyst | benzene purity | WHSV, $h^{-1}$ | benzene | methane | light HC[1] | total aromatics |
| 1 | A | 99.82 | 23.3 | 63.5 | 1.40 | 30.08 | 69.80 |
| 2 | B | 99.82 | 21.8 | 64.9 | 1.39 | 29.41 | 70.45 |
| 3 | C | 99.82 | 9.5 | 64.6 | 1.13 | 29.95 | 69.90 |
| 4 | D | 99.82 | 2.8 | 62.2 | 1.33 | 33.3 | 66.52 |

[1]light HC = $C_1$-$C_5$ hydrocarbons

The WHSV obtainable for reaching the purity of benzene of 99.82 wt % decreases as the $SiO_2/Al_2O_3$ ratio is increased. It can be seen that the methane proportion in the effluent decreases as the $SiO_2/Al_2O_3$ ratio increases from 23 to 50 and then increases as the ratio increases from 50 to 80. That is, methane in the effluent is the least when the $SiO_2/Al_2O_3$ ratio is about 50. The $SiO_2/Al_2O_3$ ratio of 25-75 therefore achieves the desired benzene purity of 99.82 wt % with an optimum benzene and total aromatics and a low methane proportion in the product stream while allowing a high WHSV. Further, the $SiO_2/Al_2O_3$ ratio of 35-75 achieves a very low methane proportion.

Effect of Pt Content

Catalysts E-K

Catalysts E-K were prepared by using the same procedure that was described for catalyst C above but the Pt contents of the catalysts were varied by ion-exchanging the HZSM-5 extrudates (the $SiO_2/Al_2O_3$ of the zeolite powder was 50) with different amounts of Pt containing solutions. Pt contents of the final catalysts are shown in Table 3. Catalysts were dried and calcined by using the same procedure. These catalysts were used in cracking of the hydrocarbon feedstock in examples 5-13.

TABLE 3

| Catalyst | SiO$_2$/Al$_2$O$_3$ Ratio[1] | Pt, wt % |
|---|---|---|
| E | 50 | 0.03 |
| F | 50 | 0.05 |
| G | 50 | 0.067 |
| H | 50 | 0.070 |
| I | 50 | 0.072 |
| J | 50 | 0.15 |
| K | 50 | 0.25 |

[1]SiO$_2$/Al$_2$O$_3$ ratio of HZSM-5 powder prior to forming extrudate measured by XRF.

Example 5

Catalyst E, weight 0.10 g
Catalyst pretreatment: same as described in example 1
Hydrocarbon feed composition and rate: same as described in example 1.
Hydrocarbon feed rate varied from 16.5 to 20.6 μl/min to run at WHSV 7.57 to 9.44 h$^{-1}$.
H$_2$ (+H$_2$S) rate: varied as described in example 1
Catalyst bed temperature 470° C., pressure 200 psig Example 6

Catalyst F, weight 0.10 g
Catalyst pretreatment: same as described in example 1
Hydrocarbon feed composition and rate: same as described in example 1.
Hydrocarbon feed rate varied from 20.6 to 24.7 μl/min to run at WHSV 9.91 to 11.89 h$^{-1}$.
H$_2$ (+H$_2$S) rate: varied as described in example 1
Catalyst bed temperature 470° C., pressure 200 psig Example 7

Catalyst G, weight 0.10 g
Catalyst pretreatment: same as described in example 1
Hydrocarbon feed composition and rate: same as described in example 1.
Hydrocarbon feed rate varied from 20.6 to 24.7 μl/min to run at WHSV 10.01 to 12.00 h$^{-1}$.
H$_2$ (+H$_2$S) rate: varied as described in example 1
Catalyst bed temperature 470° C., pressure 200 psig Example 8

Catalyst H, weight 0.10 g
Catalyst pretreatment: same as described in example 1
Hydrocarbon feed composition and rate: same as described in example 1.
Hydrocarbon feed rate varied from 20.6 to 26.8 μl/min to run at WHSV 10.11 to 13.16 h$^{-1}$.
H$_2$ (+H$_2$S) rate: varied as described in example 1
Catalyst bed temperature 470° C., pressure 200 psig Example 9

Catalyst I, weight 0.10 g
Catalyst pretreatment: same as described in example 1
Hydrocarbon feed composition and rate: same as described in example 1.
Hydrocarbon feed rate varied from 20.6 to 26.8 μl/min to run at WHSV 10.11 to 13.16 h$^{-1}$.
H$_2$ (+H$_2$S) rate: varied as described in example 1
Catalyst bed temperature 470° C., pressure 200 psig Examples 10

Catalyst J, weight 0.10 g
Catalyst pretreatment: same
Hydrocarbon feed composition and rate: same.
Hydrocarbon feed rate varied from μl/min to run at 8.92 to 10.99 WHSV to h$^{-1}$.
H$_2$ (+H$_2$S) rate: varied as described in example 1
Catalyst bed temperature 470° C., pressure 200 psig Examples 11

Catalyst K, weight 0.10 g
Catalyst pretreatment: same
Hydrocarbon feed composition and rate: same.
Hydrocarbon feed rate varied from μl/min to run at 7.94 to 9.91 WHSV to h$^{-1}$.
H$_2$ (+H$_2$S) rate: varied as described in example 1
Catalyst bed temperature 470° C., pressure 200 psig

TABLE 4

| | | wt % | | C% in effluent | | | |
|---|---|---|---|---|---|---|---|
| Example | Catalyst | benzene purity | WHSV, h$^{-1}$ | benzene | methane | light HC[1] | total aromatics |
| 5 | E | 99.82 | 8.00 | 62.48 | 1.31 | 33.21 | 66.65 |
| 6 | F | 99.82 | 11.52 | 60.88 | 1.15 | 34.53 | 65.33 |
| 7 | G | 99.82 | 12.00 | 61.52 | 1.12 | 33.73 | 66.13 |
| 8 | H | 99.82 | 12.12 | 60.88 | 1.18 | 34.26 | 65.61 |
| 9 | I | 99.82 | 12.13 | 60.26 | 1.19 | 34.97 | 64.90 |
| 10 | J | 99.82 | 8.75 | 50.46 | 1.44 | 44.70 | 55.18 |
| 11 | K | 99.82 | 8.23 | 48.60 | 1.48 | 46.15 | 53.72 |

[1]lights C$_1$-C$_5$ hydrocarbons

Based on the hydrocracking test results on Pt/HZSM-5 catalysts the Pt amount of 0.035-0.080 wt % (around 0.05-0.072 wt %) achieves the best balance of the catalyst activity (higher WHSV is preferred for the desired benzene purity), and the contents of methane, lights, benzene and total aromatics.

The invention claimed is:
1. A process for producing benzene comprising the steps of:
   (a) providing a hydrocracking feed stream comprising C$_5$-C$_{12}$ hydrocarbons,
   (b) contacting the hydrocracking feed stream in the presence of hydrogen with a hydrocracking catalyst under process conditions including a temperature of 425-580° C., a pressure of 300-5000 kPa gauge and a Weight Hourly Space Velocity of 3-30 h$^{-1}$ to produce a hydrocracking product stream comprising BTX, and
   (c) separating the BTX from the hydrocracking product stream,
   wherein the hydrocracking catalyst comprises a shaped body comprising a zeolite, a binder and a hydrogenation metal deposited on the shaped body,
   wherein the amount of the hydrogenation metal is 0.035-0.080 wt % with respect to the total catalyst,
   wherein the zeolite is ZSM-5 having a silica to alumina molar ratio of 25-75, wherein the hydrogenation metal is platinum, and
wherein the hydrocracking catalyst comprises less than 0.01 parts tin, less than 0.02 parts lead, less than 0.01 parts bismuth and less than 0.01 parts molybdenum on the basis of 100 parts by weight of the total catalyst.

2. The process according to claim 1, wherein the zeolite has a silica to alumina molar ratio of 30-65.

3. The process according to claim 2, wherein the silica to alumina molar ratio is 35-60.

4. The process according to claim 3, wherein the silica to alumina molar ratio is 40-55.

5. The process according to claim 1, wherein the hydrocracking feed stream comprises a fresh feed stream which is first stage or multi-stage hydro-treated pyrolysis gasoline, straight run naphtha, hydrocracked gasoline, light coker naphtha and coke oven light oil, FCC gasoline, reformate or mixtures thereof.

6. The process according to claim 5, wherein the fresh feed stream has been subjected to hydrogenation, enrichment of mono-aromatic compounds, and/or depentanisation.

7. The process according to claim 5, wherein the hydrocracking feed stream comprises a stream recycled from the hydrocracking product stream.

8. The process according to claim 1, wherein the hydrocracking feed stream is provided by a process which does not involve the step of removing benzene.

9. The process according to claim 1, wherein the hydrocracking feed stream comprises 10-90 wt % of benzene.

10. The process according to claim 1, wherein the amount of the binder in the hydrocracking catalyst is 10-50 wt % with respect to the total catalyst.

11. The process according to claim 1, wherein the hydrocracking catalyst is prepared by depositing the hydrogenation metal on the shaped body by impregnation or ion exchange.

12. The process according to claim 1, wherein the hydrocracking catalyst is an extrudate having an average diameter of 0.1-3 mm.

13. The process according to claim 1, wherein the step (b) is performed at a Weight Hourly Space Velocity of at least 7 $h^{-1}$.

14. The process according to claim 1, wherein the silica to alumina molar ratio is 40-55.

15. A process for producing benzene comprising the steps of:
(a) providing a hydrocracking feed stream comprising $C_5$-$C_{12}$ hydrocarbons,
(b) contacting the hydrocracking feed stream in the presence of hydrogen with a hydrocracking catalyst under process conditions including a temperature of 425-580° C., a pressure of 300-5000 kPa gauge and a Weight Hourly Space Velocity of 3-3010 to produce a hydrocracking product stream comprising BTX, and
(c) separating the BTX from the hydrocracking product stream,
wherein the hydrocracking catalyst comprises a shaped body comprising a zeolite, a binder and a hydrogenation metal deposited on the shaped body,
wherein the amount of the hydrogenation metal is 0.035-0.080 wt % with respect to the total catalyst,
wherein the zeolite is ZSM-5 having a silica to alumina molar ratio of 25-75,
wherein the hydrocracking catalyst comprises less than 0.01 parts molybdenum on the basis of 100 parts by weight of the total catalyst, and
wherein the hydrocracking catalyst comprises less than 0.01 parts tin, less than 0.02 parts lead, and less than 0.01 parts bismuth on the basis of 100 parts by weight of the total catalyst.

16. The process according to claim 15, wherein the amount of the binder in the hydrocracking catalyst is 10-50 wt % with respect to the total catalyst.

17. The process according to claim 15, wherein the zeolite has a silica to alumina molar ratio of 40-55.

* * * * *